(12) United States Patent
Halmann et al.

(10) Patent No.: US 11,229,420 B2
(45) Date of Patent: Jan. 25, 2022

(54) METHOD AND SYSTEM FOR TRACKING AN ANATOMICAL STRUCTURE OVER TIME BASED ON PULSED-WAVE DOPPLER SIGNALS OF A MULTI-GATED DOPPLER SIGNAL

(71) Applicant: General Electric Company, Schenectady, NY (US)

(72) Inventors: Menachem Halmann, Wauwatosa, WI (US); Alexander Sokulin, Tirat Carmel (IL); Peter Lysyansky, Haifa (IL); Cynthia A. Owen, Powhatan, AR (US); Dani Pinkovich, Tirat Carmel (IL)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 470 days.

(21) Appl. No.: 16/193,888

(22) Filed: Nov. 16, 2018

(65) Prior Publication Data
US 2020/0155124 A1  May 21, 2020

(51) Int. Cl.
*A61B 8/00* (2006.01)
*A61B 8/08* (2006.01)

(52) U.S. Cl.
CPC ............ *A61B 8/543* (2013.01); *A61B 8/0891* (2013.01); *A61B 8/463* (2013.01); *A61B 8/469* (2013.01);
(Continued)

(58) Field of Classification Search
CPC ....... A61B 8/543; A61B 8/0891; A61B 8/463; A61B 8/469; A61B 8/488; A61B 8/5246;
(Continued)

(56) References Cited

U.S. PATENT DOCUMENTS

| | | | |
|---|---|---|---|
| 4,819,652 A | * | 4/1989 | Micco ...................... A61B 8/06 600/455 |
| 5,365,929 A | * | 11/1994 | Peterson .................. A61B 8/06 128/916 |

(Continued)

FOREIGN PATENT DOCUMENTS

| | | | |
|---|---|---|---|
| EP | 1152364 A2 | * | 11/2001 |
| EP | 1189074 A2 | * | 3/2002 |

OTHER PUBLICATIONS

Avdal, Jorgen, "Model-Based Evaluation of Blood Velocity Estimation Techniques," Dec. 2014, 104 pages, Thesis for the degree of Philosophiae Doctor, Norwegian University of Science and Technology, Faculty of Medicine, Department of Circulation and Medical Imaging, NTNU Innovation and Creativity.
(Continued)

*Primary Examiner* — Boniface N Nganga
(74) *Attorney, Agent, or Firm* — McAndrews, Held & Malloy, Ltd.; Jacob Groethe; David Bates (57) ABSTRACT

A system and method for tracking an anatomical structure over time based on Pulsed-Wave (PW) Doppler signals of a Multi-Gated Doppler (MGD) signal is provided. The method may include identifying a gate corresponding with a selected anatomical structure. The method may include analyzing an MGD signal to track the selected anatomical structure over an extended period of time by selecting, at a plurality of sample times during the extended period of time, a PW Doppler signal from a plurality of PW Doppler signals of the MGD signal. Each of the selected PW Doppler corresponds with the selected anatomical structure at the particular sample time. The method may include presenting a continuous PW Doppler signal generated from each of the PW Doppler signals selected at each of the sample times during the extended period of time at a display system.

18 Claims, 5 Drawing Sheets

(52) U.S. Cl.
CPC ............ *A61B 8/488* (2013.01); *A61B 8/5246* (2013.01); *A61B 8/5276* (2013.01)

(58) Field of Classification Search
CPC ... A61B 8/5276; G01S 15/66; G01S 15/8925; G01S 15/8979; G01S 7/52073; G01S 7/52074; G01S 7/52085; G01P 5/244
See application file for complete search history.

(56) References Cited

U.S. PATENT DOCUMENTS

| | | | |
|---|---|---|---|
| 6,390,984 B1* | 5/2002 | Pan | A61B 8/06 600/453 |
| 9,084,576 B2 | 7/2015 | Guracar | |
| 2014/0018680 A1* | 1/2014 | Guracar | A61B 8/54 600/440 |
| 2015/0201904 A1* | 7/2015 | Guracar | A61B 8/06 600/441 |
| 2017/0086780 A1 | 3/2017 | Sokulin et al. | |

OTHER PUBLICATIONS

Kaji, T., et al., Letters to the Editor, "Simultaneous Recordings of Pulsed Wave Doppler Signals in Hepatic Vein and Descending Aorta Using Dual Doppler: A Novel Method for Evaluating Fetal Arrhythmias," Ultrasound Obstet Gynecol 2012, vol. 39, pp. 357-360, published by John Wiley & Sons, Ltd.

Von Kruger, MA, et al., "Doppler Ultrasound Tracking Instrument for Monitoring Blood Flow Velocity" Abstract, Ultrasound Med. Biol., Nov.-Dec. 2002, 1 page, as seen on website https://www.ncbi.nlm.nih.gov/pubmed/12498946 on Nov. 12, 2018.

Fredriksen, Tonje D. et al., "2-D Tracking Doppler: A New Method to Limit Spectral Broadening in Pulsed Wave Doppler," vol. 60, No. 9, Sep. 2013, pp. 1896-1905, IEEE Transactions on Ultrasonics, Ferroelectrics, and Frequency Control.

Talhami, et al., Maximum likelihood frequency tracking of the audio pulsed Doppler ultrasound signal using a halman filter, vol. 14, Issue 7, 1988, pp. 599-609, as can be on website https://www.sciencedirect.com/science/article/oii/0301562988901287 on Nov. 21, 2018.

* cited by examiner

METHOD AND SYSTEM FOR TRACKING AN ANATOMICAL STRUCTURE OVER TIME BASED ON PULSED-WAVE DOPPLER SIGNALS OF A MULTI-GATED DOPPLER SIGNAL

FIELD

Certain embodiments relate to ultrasound imaging. More specifically, certain embodiments relate to a method and system for tracking an anatomical structure over time based on Pulsed-Wave (PW) Doppler signals of a Multi-Gated Doppler (MGD) signal.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Pulsed-Wave (PW) Doppler signals are rich signals that describe the spectrum of tissue and fluid velocities in a small volume from which the signals are acquired. During an ultrasound examination of a patient, it may be desirable to inspect the PW Doppler signal of a specific anatomical structure, such as a blood vessel of interest or a segment of body tissue. The ultrasound operator performing the examination may attempt to collect the PW Doppler signal over an extended period of time, such as over the course of multiple heart or breathing cycles, to observe the periodic characteristics of the velocities in the region of interest. However, acquiring the PW signal over an extended period may be challenging, even to an experienced operator, due to movement of the patient and/or probe. For example, if an ultrasound operator is attempting to acquire PW Doppler signals of a small vessel over time, even small movements of the patient or probe can make the vessel leave the small PW Doppler signal acquisition region. As another example, if an ultrasound operator is attempting to acquire PW Doppler signals corresponding to velocities in a tissue segment, the movement of the tissue segment being examined may be greater than the small PW Doppler signal acquisition region.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for tracking an anatomical structure over time based on Pulsed-Wave (PW) Doppler signals of a Multi-Gated Doppler (MGD) signal, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for tracking an anatomical structure over time based on Pulsed-Wave (PW) Doppler signals of a Multi-Gated Doppler (MGD) signal. Various embodiments have the technical effect of providing enhanced visualization of a continuous PW Doppler signal corresponding to a tracked anatomical structure. Moreover, certain embodiments have the technical effect of generating a PW Doppler signal corresponding to a selected anatomical structure based on an MGD signal. Furthermore, aspects of the present disclosure have the technical effect of performing vessel segmentation based on the PW Doppler signals of an MGD signal such that the shape, length, and orientation may be automatically calculated. The two-dimensional (2D) shape of the vessel may be used to estimate a 2D flow velocity inside the vessel.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD, CW where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
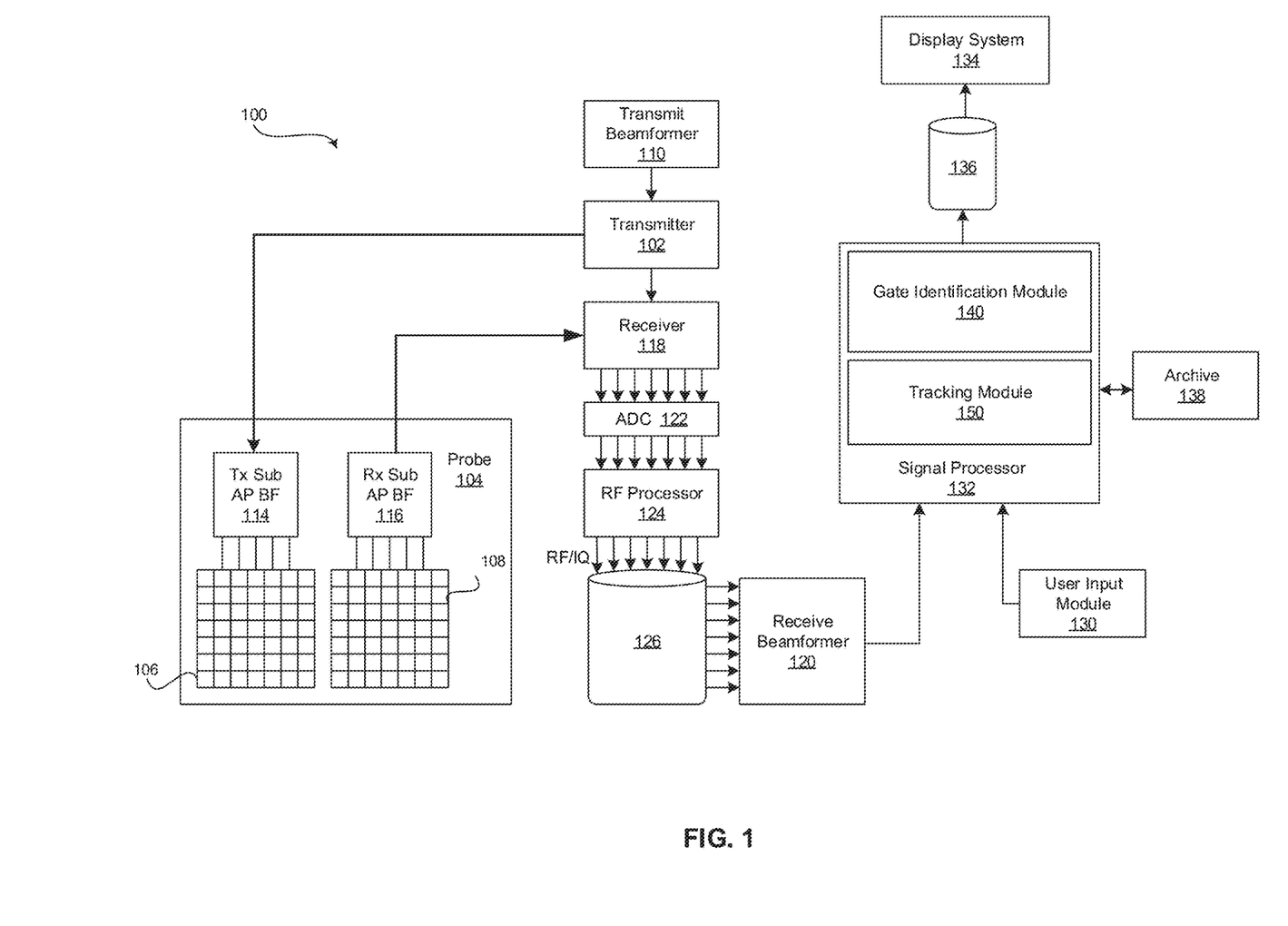
FIG. 1 is a block diagram of an exemplary ultrasound system that is operable to track an anatomical structure over time based on Pulsed-Wave (PW) Doppler signals of a Multi-Gated Doppler (MGD) signal, in accordance with various embodiments.

FIG. 1 is a block diagram of an exemplary ultrasound system 100 that is operable to track an anatomical structure over time based on PW Doppler signals 321-326, 400a-b of a Multi-Gated Doppler (MGD) signal 320, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120. Each of the receive beamformers 120 may be configured to perform digital beamforming to generate one of a plurality of PW Doppler signals that together form an MGD Doppler signal.

The user input module 130 may be utilized to input patient data, scan parameters, settings, select protocols and/or templates, activate Doppler tracking functionality, select an anatomical structure associated with a gate of an MGD signal, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the display system 134, and/or the archive 138. The user input module 130 may include button(s), rotary encoder(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display. In various embodiments, Doppler tracking functionality may be activated in response to a directive received via the user input module 130. In certain embodiments, an anatomical structure in a 2D image that corresponds to a gate of an MGD signal may be selected in response to a directive received via the user input module 130. In a representative embodiment, a 2D image and corresponding MGD ultrasound data of a region of interest may be retrieved in response to a directive received via the user input module 130.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise a gate identification module 140 and a tracking module 150.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a gate identification module 140 that comprises suitable logic, circuitry, interfaces and/or code that may be operable to identify a gate corresponding to a manually or automatically selected anatomical structure in a region of interest of a 2D ultrasound image. For example, the anatomical structure may be manually selected based on a user selection in the 2D ultrasound image via the user input module 130. As another example, the anatomical structure may be automatically selected based on the gate identification module 140 applying image detection algorithms to the 2D ultrasound image to identify a default or user specified anatomical structure. The 2D ultrasound image may be a B-mode image, color Doppler image, or any suitable 2D image, being acquired by the ultrasound system 100. Additionally and/or alternatively, the 2D ultrasound image and corresponding MGD signals may be retrieved from an archive 138, or any suitable data storage medium.

Figure 3:
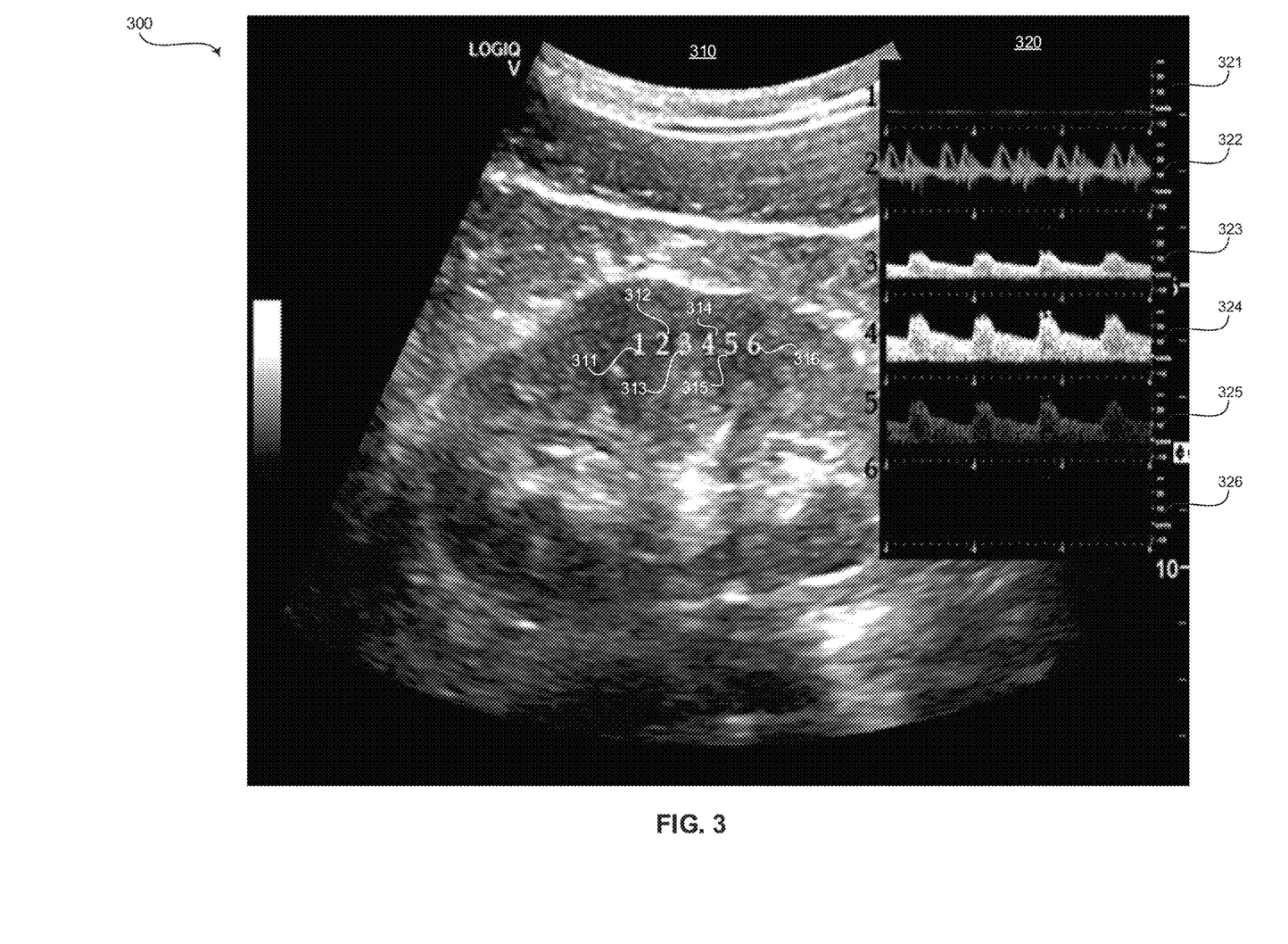
FIG. 3 illustrates an exemplary 2D image having gate locations that correspond to PW Doppler signals of an MGD signal, in accordance with various embodiments.

FIG. 3 illustrates an exemplary 2D image 310 having gate locations 311-316 that correspond to PW Doppler signals 321-326 of an MGD signal 320, in accordance with various embodiments. Referring to FIG. 3, a display system 134 may present a display 300 having a 2D ultrasound image 310 and an MGD signal 320. MGD allows simultaneous acquisition of PW Doppler signals 321-326 from many locations (i.e., gates 311-316). At least a portion of the pixels in the 2D ultrasound image 310 may correspond with different gates 311-316 of an MGD signal 320. Although 6 gates 311-316 are labeled in FIG. 3, any suitable number of gates may be implemented, such as 10 gates, 16 gates, or in a preferred embodiment, 256 gates. Each of the gates 311-316 may be associated with locations of a pixel or group of pixels in the 2D ultrasound image 310. The MGD signal 320 may comprise PW Doppler signals 321-326 corresponding to each gate of the MGD signal 320.

Referring to FIGS. 1 and 3, MGD signals 320 may be acquired with 2D images 310 and/or after identification of a gate 311-316 in the 2D image 310. In various embodiments, acquired 2D images 310 and MGD signals 320 may be stored in archive 138 or any suitable data storage medium for retrieval and post-processing. In an exemplary embodiment, the gate identification module 140 may identify a gate 311-316 corresponding to a selected anatomical structure in the 2D ultrasound image 310. For example, an operator may manually select or the gate identification module 140 may automatically select anatomical structure at a location of gate 4 314 in the 2D ultrasound image 310. The anatomical structure may be a blood vessel, segment of moving tissue, or any suitable anatomical structure. The identified gate 314 may be provided to the tracking module 150 for tracking the anatomical structure associated with the identified gate 314 and providing a PW Doppler signal 324 corresponding with the tracked anatomical structure at the display system 134 as described in more detail below.

The signal processor 132 may include a tracking module 150 that comprises suitable logic, circuitry, interfaces and/or code that may be operable to analyze an MGD signal 320 to track the anatomical structure associated with the gate 311-316 identified by the gate identification module 140. For example, the gate identification module 140 may identify a gate 311-316 corresponding with a small blood vessel having slow blood flow. During acquisition of MGD signals 320 over time, the blood vessel may move outside of the acquisition area of the originally identified gate into one or more different gates during the acquisition period due to movement of the patient or probe. The tracking module 150 may analyze the MGD signal 320 of the current frame and compare it to previously acquired MGD signal(s) 320 corresponding with the selected anatomical structure to determine the current location of the selected anatomical structure. The current location of the selected anatomical structure may be the same gate as the previous frame or a different gate from the previous frame if, for example, the patient or probe has moved. The tracking module 150 may present the appropriate PW Doppler signal 321-326 corresponding with the gate currently associated with the selected anatomical location at the display system 134. In this way, a continuous PW Doppler signal may be presented over time by the tracking module 150 stitching together the appropriate PW Doppler signal from the gate associated with the selected anatomical structure at each sample time during the acquisition period.

Figure 4:
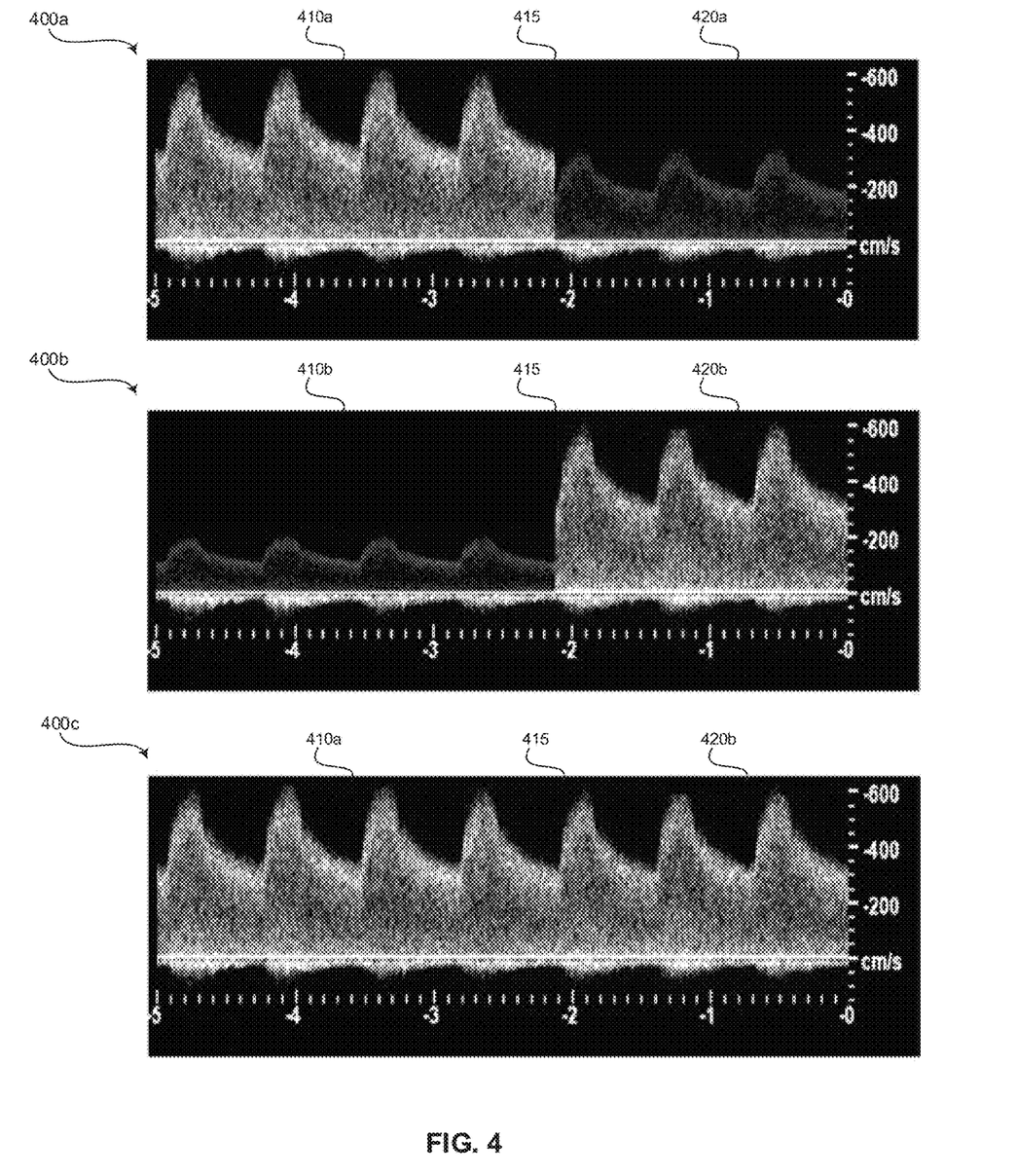
FIG. 4 is an exemplary display of a continuous PW Doppler signal corresponding to a tracked anatomical structure, the continuous PW Doppler signal generated from a first PW Doppler signal from a first gate and a second PW Doppler signal from a second gate of an MGD signal, in accordance with various embodiments.

FIG. 4 is an exemplary display of a continuous PW Doppler signal 400c corresponding to a tracked anatomical structure, the continuous PW Doppler signal 400c generated from a first PW Doppler signal 400a from a first gate and a second PW Doppler signal 400b from a second gate of an MGD signal, in accordance with various embodiments. Referring to FIG. 4, a first PW Doppler signal 400a, a second PW Doppler signal 400b, and a continuous PW Doppler signal 400c is shown. The first PW Doppler signal 400a may correspond with a first gate of an MGD signal acquired over the acquisition period. The first PW Doppler signal 400a includes a first PW Doppler signal portion 410a corresponding with a selected anatomical structure during a first time period of the acquisition period, a second PW Doppler signal portion 420a corresponding with a non-selected anatomical structure during a second time period of the acquisition period, and a point in time 415 during the acquisition period when the selected anatomical structure moved outside of the acquisition area of the first gate. The second PW Doppler signal 400b includes a first PW Doppler signal portion 410b corresponding with a non-selected anatomical structure during a first time period of the acquisition period, a second PW Doppler signal portion 420b corresponding with a selected anatomical structure during a second time period of the acquisition period, and a point in time 415 during the acquisition period when the selected anatomical structure moved into the acquisition area of the second gate. The continuous PW Doppler signal 400c may be generated by the tracking module 150 from the PW Doppler signal portions 410a, 420b that correspond to the selected anatomical structure during the acquisition period. For example, the continuous PW Doppler signal 400c of FIG. 4 includes the first PW Doppler signal portion 410a of the first PW Doppler signal 400a corresponding with the selected anatomical structure during the first time period of the acquisition period and the second PW Doppler signal portion 420b of the second PW Doppler signal 400b corresponding with the selected anatomical structure during the second time period of the acquisition period. The continuous PW Doppler signal 400c of FIG. 4 is stitched together from the first PW Doppler signal portion 410a of the first PW Doppler signal 400a and the second PW Doppler signal portion 420b of the second PW Doppler signal 400b at the point in time 415 during the acquisition period when the selected anatomical structure moved from the acquisition area of the first gate to the acquisition area of the second gate. Accordingly, despite the movement of the blood vessel, a single, continuous PW signal 400c corresponding with the selected anatomical structure over an extended acquisition time period may be presented at a display system 134.

Referring again to FIG. 1, the tracking module 150 of the signal processor 132 may track the location of the selected anatomical structure based on the MGD signal 320. For example, MGD signal 320 is obtained at many locations in the 2D ultrasound image 310 to understand where the selected anatomical structure has moved in time. In various embodiments, the MGD signal 320 for a frame at time 0 is an M×N×D matrix where M,N are the horizontal and vertical dimensions that indicates the gates at which PW Doppler signals are acquired and D is the number of velocities for which the spectrum is measured. The horizontal and vertical dimensions M,N may be mapped to provide the image coordinates X,Y of the 2D ultrasound image for each gate location where a PW Doppler signal is acquired as follows: f:[M,N]→[X,Y]. The tracking module 150 may search for a three-dimensional (3D) patch in the MGD matrix D1 (matrix at time 1) of dimensions [M×N×D] that is most similar to the patch of the same dimensions in MGD matrix D0 (matrix at time 0), which is centered around the selected anatomical structure located at coordinates (X0,Y0) at time 0 (t0) after inverse mapping is performed. The similarity may be measured using the minimal sum of square differences, the minimal sum of absolute difference, or any suitable technique. The result of the comparison identifies the PW Doppler signal associated with the gate corresponding with the image coordinates (X1,Y1) in the 2D ultrasound image at time 1 (t1). The tracking module 150 may repeat the process for subsequent frames to identify the PW Doppler signal associated with the gate corresponding with the image coordinates (X2,Y2), (X3,Y3), etc. in the 2D ultrasound image at corresponding times 2 (t2), 3 (t3), etc.

In various embodiments, the tracking performed by the tracking module 150 based on the MGD signal may be weighted with other cues to provide a more robust analysis to increase confidence of the accuracy of identifying the appropriate PW Doppler signal 321-326 corresponding with the selected anatomical structure. For example, temporal consistency and an appearance of a patch surrounding the selected anatomical structure may be cues considered by the tracking module 150 to supplement the analysis of the MGD signal 320. As an example, at an initial time (t0) in an initial 2D brightness image frame (I0), an anatomical structure located at coordinates (X0,Y0) is selected to be tracked throughout an extended acquisition period. The tracking module 150 may be configured to weigh several cues to determine where the anatomical structure at location (X0,Y0) at time (t0) moved at a next sample time (t1) in a subsequent 2D brightness image (I1). The translation of the anatomical structure between frames I0 and I1 is minimal at least because the frames are milliseconds apart and movements of the patient and/or probe are much slower. As the anatomical structure of interest moves in the ultrasound image plane due to patient and/or probe movement, it moves together with a larger patch of the image, which may be as large as the whole image. Accordingly, in various embodiments the tracking module 150 may identify an n-by-n pixels patch in the 2D brightness image frame I1 that is most similar to a corresponding patch of the same size in the 2D brightness image frame I0 centered around the original point of interest location (X0,Y0). The tracking module 150 may be configured to identify the most similar patch based on the maximal normalized cross-correlation, the minimal sum of absolute differences, or maximization of any suitable similarity measure. In certain embodiments and in a similar manner, the tracking module 150 may additionally and/or alternatively identify a patch in a color Doppler image frame (C1) which is most similar to the patch in an original color Doppler image frame (C0) around the original coordinates (X0,Y0) to serve as an additional and/or alternative cue as to where the selected anatomical structure is located.

In certain embodiments, if the selected anatomical structure is a blood vessel, for example, the tracking module 150 may track the location of the blood vessel based on the MGD signal 320 by using the periodicity of blood flow in the target vessel. For example, the ultrasound system 100 may be configured to acquire and record a three-dimensional (3D) B-mode signal corresponding to a matrix [M×N×T] and a four-dimensional (4D) PW Doppler signal corresponding to a matrix [M×N×D×T], where T is time, over a plurality of breathing and/or cardiac cycles from the approximate location of the blood vessel of interest. The tracking module 150 may be configured to track the target vessel over time, even if the target vessel moves in the 3D B-mode image because the Doppler gate 321-326 positioned on the target vessel provides a similar spectrum time signature over the acquisition period. In a representative embodiment, the tracking module applies one or more techniques to improve, locate, and track the PW Doppler signal of the selected anatomy. For example, the tracking module 150 may be configured to select a gate 311-316 and corresponding PW Doppler signal 321-326, 400*a-b* for each frame to construct a continuous PW Doppler signal 400*c* for the selected anatomical structure.

The gate may be selected by the tracking module 150 based on one or more criterion, such as PW Doppler signal strength, velocity, manual selection, spectrum tracking, cycle tracking, B-mode tracking, and/or combinations of the criterion. For example, the tracking module 150 may select the gate based on a strongest PW Doppler signal strength by choosing in each sample time the gate that produces the maximal sum of absolute or squared spectrum values. As another example, the tracking module 150 may select the gate based on a highest velocity and/or laminar flow. In an exemplary embodiment, the tracking module 150 may select the gate in response to a user input via the user input module 130 refining the automatic gate selection to obtain the desired PW Doppler signal over time. In a representative embodiment, the tracking module 150 may be configured to select the gate corresponding to the PW Doppler signal having the closest spectrum to the previous PW Doppler signal by applying a mean squared error or any suitable signal comparison technique. In certain embodiments, the tracking module 150 may select the gate corresponding to the selected anatomical structure at a current time sample in a current heart and/or breathing cycle based on a comparison with the PW Doppler signal from a corresponding time sample in a previous heart and/or breathing cycle. In various embodiments, the tracking module 150 may select the gate having a surrounding appearance in a current B-mode image frame that is closest in appearance to the surrounding appearance of the selected anatomical structure in the original B-mode image by applying the mean squared error, or any suitable localization or tracking algorithm, to patches in the B-mode images. In certain embodiments, the tracking module 150 may apply a plurality of the above-mentioned criterion to select the gate corresponding to the selected anatomical location. For example, the tracking module 150 may weigh the resemblance of the B-mode image frame features and the spectrum tracking to select the appropriate gate at the current time.

The signal processor 132 may be configured to improve the PW Doppler signal corresponding to the selected anatomical structure over the extended acquisition time period by applying temporal statistics to average the PW Doppler signal, reduce noise, reject outliers, and the like. In various embodiments, the tracking module 150 may provide information regarding the tracked anatomical structure to other clinical applications for estimating the movement of the anatomical structure over time.

In an exemplary embodiment, the signal processor 132 may perform vessel segmentation by automatically calculating the shape, length, and orientation of a vessel based on an identification of the gate locations having a similar PW Doppler signal at a given time. The signal processor 132 may be configured to estimate the 2D flow velocity inside the vessel once the 2D shape of the vessel is known, which is an improvement on the velocity component parallel to the line-of-sight that is typically available using the Doppler effect.

Figure 2:
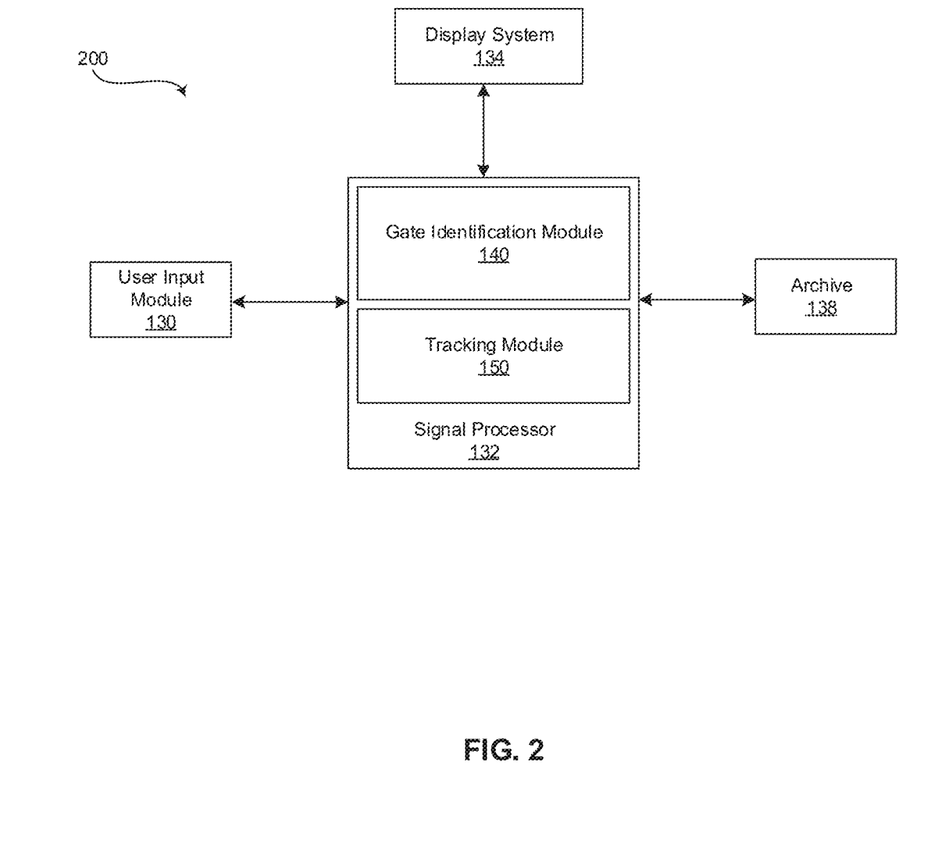
FIG. 2 is a block diagram of an exemplary medical workstation that is operable to track an anatomical structure over time based on PW Doppler signals of an MGD signal, in accordance with various embodiments.

FIG. 2 is a block diagram of an exemplary medical workstation 200 that is operable to track an anatomical structure over time based on PW Doppler signals 321-326, 400*a-b* of an MGD signal 320, in accordance with various embodiments. In various embodiments, components of the medical workstation 200 may share various characteristics with components of the ultrasound system 100, as illustrated in FIG. 1 and described above. Referring to FIG. 2, the medical workstation 200 comprises a display system 134, a signal processor 132, an archive 138, and a user input module 130, among other things. Components of the medical workstation 200 may be implemented in software, hardware, firmware, and/or the like. The various components of the medical workstation 200 may be communicatively linked. Components of the medical workstation 200 may be implemented separately and/or integrated in various forms. For example, the display system 134 and the user input module 130 may be integrated as a touchscreen display.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as B-mode images 310, color Doppler images, PW Doppler signals 321-326, 400*a-c*, or any suitable information.

The signal processor 132 may be one or more central processing units, microprocessors, microcontrollers, and/or the like. The signal processor 132 may be an integrated component, or may be distributed across various locations, for example. The signal processor 132 comprises a gate identification module 140 and a tracking module 150, as described above with reference to FIG. 1, and may be capable of receiving input information from a user input module 130 and/or archive 138, generating an output displayable by a display system 134, and manipulating the output in response to input information from a user input module 130, among other things. The signal processor 132, gate identification module 140, and/or tracking module 150 may be capable of executing any of the method(s) and/or set(s) of instructions discussed herein in accordance with the various embodiments, for example.

The archive 138 may be one or more computer-readable memories integrated with the medical workstation 200 and/or communicatively coupled (e.g., over a network) to the medical workstation 200, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data and instructions for tracking an anatomical structure over time based on Pulsed-Wave (PW) Doppler signals 321-326, 400a-b of a Multi-Gated Doppler (MGD) signal 320, for example.

The user input module 130 may include any device(s) capable of communicating information from a user and/or at the direction of the user to the signal processor 132 of the medical workstation 200, for example. As discussed above with respect to FIG. 1, the user input module 130 may include a touch panel, button(s), a mousing device, keyboard, rotary encoder, trackball, camera, voice recognition, and/or any other device capable of receiving a user directive.

Figure 5:
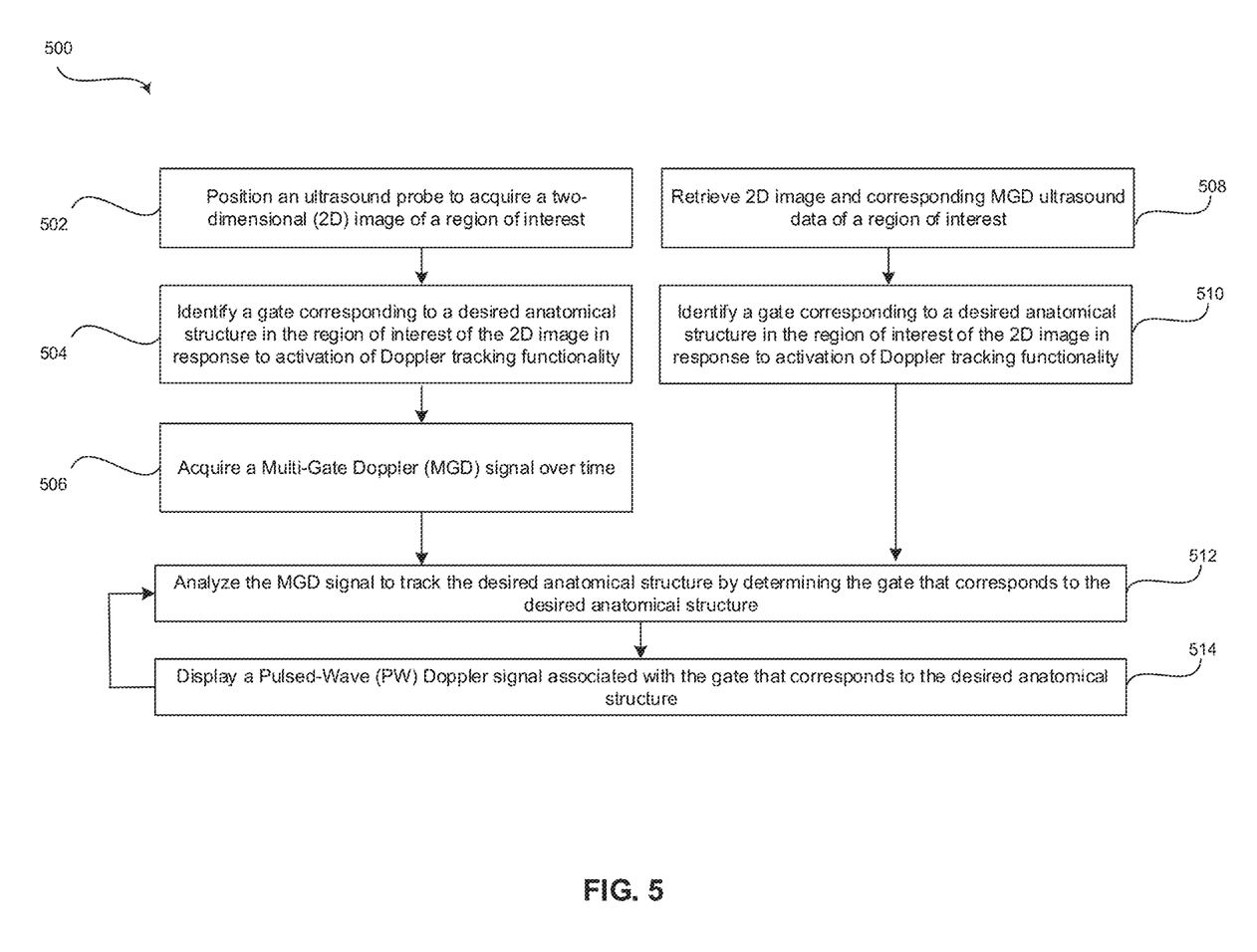
FIG. 5 is a flow chart illustrating exemplary steps that may be utilized for tracking an anatomical structure over time based on PW Doppler signals of an MGD signal, in accordance with exemplary embodiments.

FIG. 5 is a flow chart illustrating exemplary steps 500 that may be utilized for tracking an anatomical structure over time based on PW Doppler signals 321-326, 400a-b of an MGD signal 320, in accordance with exemplary embodiments. Referring to FIG. 5, there is shown a flow chart 500 comprising exemplary steps 502 through 514. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 502, a probe 104 of an ultrasound system 100 may be positioned to acquire a two-dimensional (2D) image 310 of a region of interest. For example, the ultrasound system 100 may acquire the 2D image 310 with an ultrasound probe 104 positioned over a region of interest, such as a blood vessel, heart, or any suitable anatomical structure.

At step 504, the signal processor 132 of the ultrasound system 100 may identify a gate 311-316 corresponding to a desired anatomical structure in the region of interest of the 2D image 310 in response to activation of Doppler tracking functionality. For example, a gate identification module 140 of the signal processor 140 may receive an instruction via user input module 130 to activate Doppler tracking functionality. Once Doppler tracking functionality is activated, the gate identification module 140 may identify a gate 311-316 corresponding to a selected anatomical structure in the 2D image 310. As an example, the anatomical structure may be manually selected based on a user selection in the 2D ultrasound image via the user input module 130. As another example, the anatomical structure may be automatically selected based on the gate identification module 140 applying image detection algorithms to the 2D ultrasound image 310 to identify a default or user-specified anatomical structure. The identified gate 314 may be provided to a tracking module 150 of the signal processor 132.

At step 506, the ultrasound system 100 may acquire a MGD signal 320 over time. For example, the ultrasound probe 104 positioned over the region of interest may acquire PW Doppler signals 321-326 forming an MGD signal 320 over an extended acquisition period. The acquisition period may correspond with a number of heart and/or breathing cycles.

At step 508, a signal processor 132 may retrieve 2D image 310 and corresponding MGD ultrasound data 320 of a region of interest. For example, the signal processor 132 of a workstation 200 or ultrasound system 100 may retrieve the 2D images 310 and corresponding MGD ultrasound data 320 from an archive 138 or any suitable data storage medium.

At step 510, the signal processor 132 of the ultrasound system 100 or workstation 200 may identify a gate 311-316 corresponding to a desired anatomical structure in the region of interest of the retrieved 2D image 310 in response to activation of Doppler tracking functionality. For example, a gate identification module 140 of the signal processor 140 may receive an instruction via user input module 130 to activate Doppler tracking functionality. Once Doppler tracking functionality is activated, the gate identification module 140 may identify a gate 311-316 corresponding to a selected anatomical structure in the 2D image 310. As an example, the anatomical structure may be manually selected based on a user selection in the 2D ultrasound image via the user input module 130. As another example, the anatomical structure may be automatically selected based on the gate identification module 140 applying image detection algorithms to the 2D ultrasound image 310 to identify a default or user-specified anatomical structure. The identified gate 314 may be provided to a tracking module 150 of the signal processor 132.

At step 512, the signal processor 132 may analyze the MGD signal 320 to track the desired anatomical structure by determining the gate 311-316 that corresponds to the desired anatomical structure. For example, the tracking module 150 of the signal processor 132 may analyze a current MGD signal 320 and compare it to previously acquired MGD signal(s) 320 corresponding with the selected anatomical structure to determine the current location of the selected anatomical structure. The current location of the selected anatomical structure may correspond with the same gate as the previous frame or a different gate from the previous frame if, for example, the patient or probe has moved. The tracking module 150 may present the appropriate PW Doppler signal 321-326 corresponding with the gate currently associated with the selected anatomical location at the display system 134. The selected PW Doppler signal 321-326 may be stitched together with previous and subsequent selected PW Doppler signals 321-326 associated with the selected anatomical structure to generate a continuous PW Doppler signal 400c corresponding with the selected anatomical structure. In various embodiments, the tracking module 150 may select the gate of the current MGD signal 320 corresponding to the selected anatomical structure based on one or more criterion, such as PW Doppler signal strength, velocity, manual selection, spectrum tracking, cycle tracking, B-mode tracking, and/or combinations of the criterion. In certain embodiments, the tracking performed by the tracking module 150 based on the MGD signal 320 may be weighted with other cues, such as temporal consistency, an appearance of a patch surrounding the selected anatomical structure, and/or any suitable cues to provide a more robust analysis to increase confidence of the accuracy of identifying the appropriate PW Doppler signal 321-326 corresponding with the selected anatomical structure.

At step 514, the signal processor 132 may display a PW Doppler signal 321-326, 400a-c associated with the gate 311-316 that corresponds to the desired anatomical structure. For example, the tracking module 150 of the signal processor 132 may present the continuous PW Doppler signal 400c at a display system 134 of the ultrasound system 100 and/or workstation 200. Steps 512 and 514 may be repeated for each time sample of the MGD signal 320 to present the continuous PW Doppler signal 400c over the extended acquisition period.

Various embodiments provide a method 500 to track a specific anatomical structure based on its PW Doppler signal 400c, even if the anatomical structure moves due to patient and/or probe 104 movements. Aspects of the present disclosure solve the problem of tracking an anatomical structure over an extended period of time using a brightness image 310, color Doppler image, and/or MGD 320 that provides a PW Doppler signal 321-326, 401a-b at many locations 311-316 in the ultrasound image 310. The described system 100, 200 and method 500 solves the clinical problem of tracking the PW Doppler signal 401c of a small vessel, which in addition to being small in size also has slow blood flow. The described system 100, 200 and method 500 automatically track a vessel or tissue of interest for an extended period of time, even when the surrounding texture is smooth and/or the vessel of interest is very small. By directly tracking the region based on its PW Doppler signal 321-236, 401a-b, the PW Doppler examination is continuous 401c and taken from the correct region throughout the extended acquisition period. The present disclosure provides a commercial advantage of, among other things, the ability to track a small region of interest and obtain a PW Doppler signal 401c over an extended period of time by a less-well trained physician or technician, which increases the potential market size for ultrasound devices 100.

Aspects of the present disclosure provide a method 500 and system 100, 200 for tracking an anatomical structure over time based on PW Doppler signals 321-326, 400a-b of an MGD signal 320. In accordance with various embodiments, the method 500 may comprise identifying 504, 510, by at least one processor 132, 140, a gate 311-316 corresponding with a selected anatomical structure at an initial time. The gate may be one of a plurality of gates 311-316. Each of the plurality of gates 311-316 may correspond with one of a plurality of Pulsed-Wave (PW) Doppler signals 321-326, 400a-b that together define a Multi-Gated Doppler (MGD) signal 320. The method 500 may comprise receiving 506, 508, by the at least one processor 132, 140, 150, the MGD signal 320 over an extended period of time. The method 500 may comprise analyzing 512, by the at least one processor 132, 150, the MGD signal 320 to track the selected anatomical structure over the extended period of time by selecting, at a plurality of sample times during the extended period of time and subsequent the initial time, a PW Doppler signal 410a, 420b from the plurality of PW Doppler signals 321-326, 400a-b. Each of the PW Doppler signal 410a, 420b corresponding to one of the plurality of gates 311-316 and the selected anatomical structure. The method 500 may comprise presenting 514, at a display system 134, a continuous PW Doppler signal 400c generated from each of the PW Doppler signal 410a, 420b selected at each of the plurality of sample times during the extended period of time.

In a representative embodiment, the extended period of time includes one or both of at least one breathing cycle and at least one heart cycle. In an exemplary embodiment, the selected anatomical structure is at least one of a blood vessel or a tissue segment. In certain embodiments, the gate 311-316 is identified based on a selection of the selected anatomical structure in a two-dimensional (2D) ultrasound image 310. In various embodiments, the selection is one of: an automatic selection, by the at least one processor 132, 140, based on image detection techniques, or a manual selection in response to a user directive received via a user input module 130. In a representative embodiment, the analyzing the MGD signal 320 is weighted with at least one other cue to track the selected anatomical structure over the extended period of time. The at least one other cue may comprise one or both of temporal consistency, and an appearance of a patch in the 2D ultrasound image 310 surrounding the selected anatomical structure. In various embodiments, the MGD signal 320 is received from one or both of an ultrasound probe 104 or a data storage medium 138. In certain embodiments, the PW Doppler signal 410a, 420b is selected from the plurality of PW Doppler signals 321-326, 400a-b based on one or more of PW Doppler signal strength, velocity, a manual selection, spectrum tracking, cycle tracking, and B-mode tracking.

Various embodiments provide a system 100, 200 for tracking an anatomical structure over time based on PW Doppler signals 321-326, 400a-b of an MGD signal 320. The system 100, 200 may comprise at least one processor 132, 140, 150 and a display system 134. The at least one processor 132, 140 may be configured to identify a gate 311-316 corresponding with a selected anatomical structure at an initial time. The gate may be one of a plurality of gates 311-316. Each of the plurality of gates 311-316 may correspond with one of a plurality of PW Doppler signals 321-326 that together define an MGD signal 320. The at least one processor 132, 140, 150 may be configured to receive the MGD signal 320 over an extended period of time. The at least one processor 132, 150 may be configured to analyze the MGD signal 320 to track the selected anatomical structure over the extended period of time by selecting, at a plurality of sample times during the extended period of time and subsequent the initial time, a PW Doppler signal 410a, 420b from the plurality of PW Doppler signals 321-326, 400a-b. Each of the PW Doppler signal 410a, 420b may correspond to one of the plurality of gates 311-316 and the selected anatomical structure. The display system 134 may be configured to present a continuous PW Doppler signal 400c generated from each of the PW Doppler signal 410a, 420b selected at each of the plurality of sample times during the extended period of time.

In an exemplary embodiment, the extended period of time includes one or both of at least one breathing cycle and at least one heart cycle. In certain embodiments, the selected anatomical structure is at least one of a blood vessel or a tissue segment. In various embodiments, the gate 311-316 is identified based on a selection of the selected anatomical structure in a 2D ultrasound image 310. The selection may be one of an automatic selection, by the at least one processor 132, 140, based on image detection techniques, or a manual selection in response to a user directive received via a user input module 130. In a representative embodiment, the analyzing the MGD signal 320 may be weighted with at least one other cue to track the selected anatomical structure over the extended period of time. The at least one other cue may comprises one or both of temporal consistency, and an appearance of a patch in the 2D ultrasound image 310 surrounding the selected anatomical structure. In an exemplary embodiment, the MGD signal 320 may be received from one or both of an ultrasound probe 104 or a data storage medium 138. In various embodiments, the PW Doppler signal 410a, 420b is selected from the plurality of PW Doppler signals 321-326, 400a-b based on one or more of PW Doppler signal strength, velocity, a manual selection, spectrum tracking, cycle tracking, and B-mode tracking.

Certain embodiments provide a non-transitory computer readable medium having stored thereon, a computer program having at least one code section. The at least one code section is executable by a machine for causing the machine to perform steps 500. The steps 500 may comprise identifying 504, 510 a gate 311-316 corresponding with a selected anatomical structure at an initial time. The gate may be one of a plurality of gates 311-316. Each of the plurality of gates 311-316 may correspond with one of a plurality of PW Doppler signals 321-326, 400a-b that together define an MGD signal 320. The steps 500 may comprise receiving 506, 508 the MGD signal 320 over an extended period of time. The steps 500 may comprise analyzing 512 the MGD signal 320 to track the selected anatomical structure over the extended period of time by selecting, at a plurality of sample times during the extended period of time and subsequent the initial time, a PW Doppler signal 410a, 420b from the plurality of PW Doppler signals 321-326, 400a-b, each of the PW Doppler signal 410a, 420b corresponding to one of the plurality of gates 311-316 and the selected anatomical structure. The steps 500 may comprise presenting 514 a continuous PW Doppler signal 400c generated from each of the PW Doppler signal 410a, 420b selected at each of the plurality of sample times during the extended period of time at a display system 134.

In various embodiments, the extended period of time includes one or both of at least one breathing cycle and at least one heart cycle. The selected anatomical structure may be at least one of a blood vessel or a tissue segment. In a representative embodiment, the gate 311-316 may be identified based on a selection of the selected anatomical structure in a 2D ultrasound image 310. The selection may be one of an automatic selection based on image detection techniques, or a manual selection in response to a user directive received via a user input module 130. In an exemplary embodiment, the analyzing 512 the MGD signal 320 may be weighted with at least one other cue to track the selected anatomical structure over the extended period of time. The at least one other cue may comprises one or both of temporal consistency, and an appearance of a patch in the 2D ultrasound image 310 surrounding the selected anatomical structure. In certain embodiments, the PW Doppler signal 410a, 420b may be selected from the plurality of PW Doppler signals 321-326, 400a-b based on one or more of PW Doppler signal strength, velocity, a manual selection, spectrum tracking, cycle tracking, and B-mode tracking.

As referred to herein, the terms "substantially a same time," "substantially in real-time," and the like refer to the small amount of time offset inherent to processing delays dependent on the processing power of the at least one processor 132, 140, 150, 160. As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for tracking an anatomical structure over time based on PW Doppler signals of an MGD signal.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
identifying, by at least one processor, a gate corresponding with a selected anatomical structure at an initial time, wherein the gate is one of a plurality of gates, each of the plurality of gates corresponding with one of a plurality of Pulsed-Wave (PW) Doppler signals that together define a Multi-Gated Doppler (MGD) signal;
receiving, by the at least one processor, the MGD signal over an extended period of time;
analyzing, by the at least one processor, the MGD signal to track the selected anatomical structure over the extended period of time by selecting, at a plurality of sample times during the extended period of time and subsequent the initial time, a PW Doppler signal from the plurality of PW Doppler signals, each of the PW Doppler signal corresponding to one of the plurality of gates and the selected anatomical structure, wherein the analyzing the MGD signal is weighted with at least one other cue to track the selected anatomical structure over the extended period of time, and wherein the at least one other cue is selected from the group consisting of:
an appearance of a patch in a two-dimensional (2D) ultrasound image surrounding the selected anatomical structure,
temporal consistency and the appearance of the patch in the 2D ultrasound image surrounding the selected anatomical structure, and
a periodicity of blood flow in a blood vessel; and
presenting, at a display system, a continuous PW Doppler signal generated from each of the PW Doppler signal selected at each of the plurality of sample times during the extended period of time.

2. The method of claim 1, wherein the extended period of time includes one or both of at least one breathing cycle and at least one heart cycle.

3. The method of claim 1, wherein the selected anatomical structure is at least one of the blood vessel or a tissue segment.

4. The method of claim 1, wherein the gate is identified based on a selection of the selected anatomical structure in the 2D ultrasound image.

5. The method of claim 4, wherein the selection is one of:
an automatic selection, by the at least one processor, based on image detection techniques, or
a manual selection in response to a user directive received via a user input module.

6. The method of claim 1, wherein the MGD signal is received from one or both of an ultrasound probe or a data storage medium.

7. The method of claim 1, wherein the at least one other cue is the appearance of the patch in the 2D ultrasound image surrounding the selected anatomical structure.

8. The method of claim 1, wherein the at least one other cue is the temporal consistency and the appearance of the patch in the 2D ultrasound image surrounding the selected anatomical structure.

9. The method of claim 1, wherein the at least one other cue is the periodicity of blood flow in the blood vessel.

10. A system comprising:
at least one processor configured to:
identify a gate corresponding with a selected anatomical structure at an initial time, wherein the gate is one of a plurality of gates, each of the plurality of gates corresponding with one of a plurality of Pulsed-Wave (PW) Doppler signals that together define a Multi-Gated Doppler (MGD) signal;
receive the MGD signal over an extended period of time; and
analyze the MGD signal to track the selected anatomical structure over the extended period of time by selecting, at a plurality of sample times during the extended period of time and subsequent the initial time, a PW Doppler signal from the plurality of PW Doppler signals, each of the PW Doppler signal corresponding to one of the plurality of gates and the selected anatomical structure, wherein the analyzing the MGD signal is weighted with at least one other cue to track the selected anatomical structure over the extended period of time, and wherein the at least one other cue is selected from the group consisting of:
an appearance of a patch in a 2D ultrasound image surrounding the selected anatomical structure,
temporal consistency and the appearance of the patch in the 2D ultrasound image surrounding the selected anatomical structure, and
a periodicity of blood flow in a blood vessel; and
a display system configured to present a continuous PW Doppler signal generated from each of the PW Doppler signal selected at each of the plurality of sample times during the extended period of time.

11. The system of claim 10, wherein the extended period of time includes one or both of at least one breathing cycle and at least one heart cycle.

12. The system of claim 10, wherein the selected anatomical structure is at least one of the blood vessel or a tissue segment.

13. The system of claim 10, wherein the gate is identified based on a selection of the selected anatomical structure in the 2D ultrasound image, and wherein the selection is one of: an automatic selection, by the at least one processor, based on image detection techniques, or a manual selection in response to a user directive received via a user input module.

14. The system of claim 10, wherein the MGD signal is received from one or both of an ultrasound probe or a data storage medium.

15. The system of claim 10, wherein the at least one other cue is the appearance of the patch in the 2D ultrasound image surrounding the selected anatomical structure.

16. The system of claim 10, wherein the at least one other cue is the temporal consistency and the appearance of the patch in the 2D ultrasound image surrounding the selected anatomical structure.

17. The system of claim 10, wherein the at least one other cue is the periodicity of blood flow in the blood vessel.

18. A non-transitory computer readable medium having stored thereon, a computer program having at least one code section, the at least one code section being executable by a machine for causing the machine to perform steps comprising:
identifying a gate corresponding with a selected anatomical structure at an initial time, wherein the gate is one of a plurality of gates, each of the plurality of gates corresponding with one of a plurality of Pulsed-Wave (PW) Doppler signals that together define a Multi-Gated Doppler (MGD) signal;
receiving the MGD signal over an extended period of time;
analyzing the MGD signal to track the selected anatomical structure over the extended period of time by selecting, at a plurality of sample times during the extended period of time and subsequent the initial time, a PW Doppler signal from the plurality of PW Doppler signals, each of the PW Doppler signal corresponding to one of the plurality of gates and the selected anatomical structure, wherein the analyzing the MGD signal is weighted with at least one other cue to track the selected anatomical structure over the extended period of time, and wherein the at least one other cue is selected from the group consisting of:
an appearance of a patch in a 2D ultrasound image surrounding the selected anatomical structure,
the temporal consistency and the appearance of the patch in the 2D ultrasound image surrounding the selected anatomical structure, and
a periodicity of blood flow in a blood vessel; and
presenting a continuous PW Doppler signal generated from each of the PW Doppler signal selected at each of the plurality of sample times during the extended period of time at a display system.

* * * * *